United States Patent [19]

Chow et al.

[11] Patent Number: 5,525,148
[45] Date of Patent: Jun. 11, 1996

[54] SELF-SETTING CALCIUM PHOSPHATE CEMENTS AND METHODS FOR PREPARING AND USING THEM

[75] Inventors: Laurence C. Chow, Potomac; Shozo Takagi, Gaithersburg, both of Md.

[73] Assignee: American Dental Association Health Foundation, Chicago, Ill.

[21] Appl. No.: 126,502

[22] Filed: Sep. 24, 1993

[51] Int. Cl.$^6$ .................................................. C09K 3/00
[52] U.S. Cl. .................. 106/35; 423/308; 423/309; 423/311; 106/690; 106/691; 106/792
[58] Field of Search .................. 106/35, 690, 691, 106/792; 423/308, 311, 309, 305; 501/1; 433/180, 199.1, 201.1, 212.1, 215, 226, 228.1; 623/16

[56] References Cited

U.S. PATENT DOCUMENTS

| Re. 33,161 | 2/1990 | Brown et al. | 423/308 |
|---|---|---|---|
| Re. 33,221 | 5/1990 | Brown et al. | 423/308 |
| 3,679,360 | 7/1972 | Rubin et al. | 23/109 |
| 3,787,900 | 1/1974 | McGee | 106/35 |
| 3,913,229 | 10/1975 | Driskell et al. | 32/1 |
| 3,929,971 | 12/1975 | Roy | 423/308 |
| 4,097,935 | 7/1978 | Jarcho | 106/35 |
| 4,497,075 | 2/1985 | Niwa et al. | 423/308 |
| 4,599,085 | 7/1986 | Riess et al. | 623/16 |
| 4,880,610 | 11/1989 | Constantz | 423/305 |
| 5,034,059 | 7/1991 | Constantz | 106/161 |
| 5,047,031 | 9/1991 | Constantz | 606/77 |
| 5,053,212 | 10/1991 | Constantz et al. | 423/305 |
| 5,129,905 | 7/1992 | Constantz | 606/76 |

OTHER PUBLICATIONS

Briner, et al., "Significance of Enamel Remineralization" J. Dent. Res. 53:239–243 (1974).

Silverstone, "Remineralization Phenomena" Caries Res. 11 (Supp. 1): 59–84 (1977).

Brown, "Solubilities of Phosphates and Other Sparingly Soluble Compounds" from Griffith, et al. Environmental Phosphorous Handbook (John Wiley & Sons, New York, 1973).

Miyazaki, et al., "An Infrared Spectroscopic Study of Cement Formation of Polymeric Calcium Phosphate Cement," Journal of Japanese Society for Dental Materials and Devices, vol. II, No. 2, 1992.

Brown, et al. "Crystallography of Tetracalcium Phosphate", J. Res. Nat. Bur.Stds. 69A: 547–551 (Dec. 1965).

Brown & Chow "Singular Points in the Chemistry of Teech" IADR Abstract No. 120, J. Dent. Res. 54:74 (Feb. 1975).

Driskell, et al. "Development of Ceramic and Ceramic Composite Devices for Maxillofacial Application" J. Biomed. Mat. Res. 6: 345–361 (1972).

Gelhard et al. "Rehardening of Artificial Enamel Lesions in Vivo" Caries Res. 13: 80–83 (1979).

Gregory, et al. "Solubility of CaHPO$_4$ 2H$_2$O in the System Ca(OH)$_2$—H$_3$PO$_4$ —H$_2$O at 5, 15, 25 and 37.5°C", J. Res. Nat. Bur. Std. 74A: 461–475 (Aug. 1970).

Gregory, et al. "Solubility of — Ca$_3$(PO$_4$)$_2$ in the System Ca(OH$_2$—H$_3$PO$_4$—H$_2$O at 5, 15, 25 and 37°C", J. Res. Nat. Bur. Std. 78A: 667–674 (Dec. 1974).

Hiatt, et al. "Root Preparation I. Obduration of Dentinal Tubules in Treatment of Root Hypersensitivity" J. Periodontal 43: 373–380 (Jun. 1972).

(List continued on next page.)

Primary Examiner—Paul Marcantoni
Attorney, Agent, or Firm—Banner & Allegretti, Ltd.

[57] ABSTRACT

The invention includes methods and compositions relating to calcium phosphate cements, which self-harden substantially to hydroxyapatite at ambient temperature when in contact with an aqueous medium. More specifically the cements comprise a combination of one or more sparingly soluble calcium phosphates other than tetracalcium phosphate with an aqueous solution adjusted with a base to maintain a pH of about 12.5 or above and having sufficient dissolved phosphate salt to yield a solution mixture with phosphate concentration equal to or greater than about 0.2 mol/L.

33 Claims, 2 Drawing Sheets

OTHER PUBLICATIONS

LeGeros, et al. "Apatitic Calcium Phosphates: Possible Dental Restorative Materials" IADR Abstract No. J. Dent. Res. 1482 (1982).

Levine, "Remineralization of Natural Carious Lesions of Enamel In Vitro" Brit. Dent. J. 137: 132–34 (1974).

McDowell, et al. "Solubility of —$Ca_5(PO_4)_3$ In the System $Ca(OH)_2$—$H_3PO_4$ — $H_2O$ at 5, 15, 25 and 37°C" J. Res. Nat. Bur. Std. 81 A: 273–281 (Mar.–Jun. 1977).

McDowell, et al. "Solubility Study of Calcium Hydrogen Phosphate. Ion Pair Formation" Inorg. Chem. 10: 1638–1643 (1971).

Moreno, et al. "Stability of Dicalcium Phosphate Dihydrate in Aqueous Solutions and Solubility of Octacalcium Phosphate" Soil Sci. Soc. Am. Proc. 21:99–102 (1960).

"NASA and Dentistry" (Oct. 1977).

Patel, et al. "Solubility of $CaHPO_4$ $2H_2O$ in the Quaternary System $Ca(OH)_2$—$H_3PO_4$ NaCl — $H_2O$ at 25° C", J. Res. Nat. Bur. Std. 78A: 675–681 (1974).

Pickel, et al. "The Effect of a Chewing Gum Containing Dicalcium Phosphate On Salivary Calcium and Phosphate" Ala. J. Med. Sci. 2: 286–7 (1965).

Zimmerman, et al. "The Effect of Remineralization Fluids on Carious Lesions In Vitro" IADR Abstract No. 282 (1979).

Guide To Dental Materials and Devices 7th Ed. (ADA 1974) p. 49.

Brown, et al. (1988): "A New Calcium Phosphate, Water Setting Cement," Cements Res. Progress 1986, P. W. Brown, Ed., Westerville, Ohio: American Ceramic Society pp. 352–379.

Chohayeb, A. A. et al. (1987) "Evaluation of Calcium Phosphate as a Root Canal Sealer–Filler Material", J. Endod. 13, 384–86.

Hong, et al. (1989) "The Periapical Tissue Reactions to a Calcium Phosphate Cement in the Teeth of Monkeys," J. Dent. Res. (submittted).

Constantino, et al. (1989) "Evaluation of a New Hydroxyapatite Cement: Cranioplasty in a Cat Model", The 5th Interntl. Symposium on Facial Plastic Reconstructive Surgery of the Head and Neck, Toronto Canada.

DeRijk, et al. (1986) Clinical Evaluation of an Hydroxyapatite Precipitate for the Treatment of Dentinal Hypersensitivity, Biomed. Eng. v. Recent Developments, Proc. of 5th Southern Biomedical Engineering Conference, Subrata Saha, Ed., New York: Pergamon Press, pp. 336–339.

Grunninger et al. (1984): Evaluation of the Biocompatibility of a New Calcium Phosphate Setting Cement, J. Dent. Res. 63 (Special Issue) Abst. No. 270.

Hanker et al (1987) Calcium Phosphate Binders for Hydroxyapatite Particles for Bone Repair, J. Dent. Res. 66, Abst. No. 1144.

Lu, et al. (1988): "New Attachment Following the Use of a Novel Calcium Phosphate System" J. Dent. Res. 67: 352, Abst. No. 1913.

Schreiber, et al. (1988): "Remineralization of Root Caries Lesion by a Calcium Phosphate Slurry", J. Dent. Res. 67: Abst. No. 255.

Sugawara, et al. (1987): "A Calcium Phosphate Root Canal Sealer–Filler", J. Dent. Res. 66: 296 Abst. No. 1516.

Sugawara et al. (1989): "Formation of Hydroxyapatite in Hydrogels from Tetracalcium Phosphate/Dicalcium Phosphate Mixtures", Nihon Univ.Sch. Dent.vol. 31 No. 1, 1989.

Block, et al (1988): "Correction of Vertical Orbital Dystopia with a Hydroxyapaptite Orbital Floor Graft", J. Oral Maxillofac Surg. 84, 2:236–244, (1989).

Salyer, et al. (1989): "Porous Hydroxyapatite as an Onlay Bone–Graft Substitute for Maxillofacial Surgery", Plas. and Recon. Surg. 84, 2:236–44, 1989.

Kenney, et al. (1988): "The Use of a Porous Hydroxyapatite Implant in Periodontal Defects", J. Periodontal, 67–72 Feb., 1988.

Zide et al. (1987) "Hydroxyapatite Cranioplasty Directly Over Dura", J. Oral Maxillofac. Surg 45:481–86, 1987.

Waite, et al. (1986) Zygomatic Augmentation with Hydroxyapatite, J. Oral Maxillofac. Surg. 44: 349–352, 1986.

Verwoerd, et al (1987): "Porous Hydroxyapatite–perichondrium Graft in Cricoid Reconstruction", Acta Otolaryngol (Stockh) 1987; 103:496–502.

Grote, (1984): "Tympanoplasty With Calcium Pohsphate", Arch. Otolaryngology 110: 197–199, 1984.

Kent, et al. (1983) "Alveolar Ridge Augmentation Using Nonresorbable Hydroxyapatite With or Without Autogenous Cancellous Bone", J. Oral Maxillofac. Surg. 41:629–42, 1983.

Piecuch (1986): Augmentation of the Atrophic Edentulous Ridge with Porus Replamineform Hysroxyapatite (Interpore–200) Dent. Clinics of North America 30, 2:291–305, 1986.

Misch (1987): "Maxillary Sinus Augmentation for Endosteal Implants: Organized Alternative Treatment Plans", Int. J. Oral Implant 4, 2:49–58, 1987.

Chow, L. C., "Calcium Phosphate Materials: Reactor Response" Adv. Dent. Res. 2(1): 191–184, Aug. 1988.

Fukase, et al. "Setting Reactions and Compressive Strengths of Calcium Phosphate Cements" J. Dent. Res. 69 (12): 1852–56, Dec. 1990.

Chow, Development of Self-Setting Calcium Phosphate Cements, J. of the Ceramic Society of Japan, 99(10)954–64 (1991).

Chow, et al. "Self–Setting Calcium Phosphate Cements," Mat. Res. Soc. Symp. Proc. vol. 179, (1991).

Miyazaki, et al "Chemical Change of Hardened PCA/CPC Cements in Various Storing Solutions", The J. of the Japanese Soc. for Den. Mats & Devices, vol. 11, No. 2, (1992).

Fukase et al "Thermal Conductivity of Calcium Phosphate Cement," IADR Abt. (1990).

Sugawara, et al. "Biocompatibility and Osteoconductivity of Calcium Phosphate Cement" IADR Abstract (1990).

Miyazaki, et al. "Polymeric Calcium Phosphate Cements" IADR Abst. (1990).

Sugawara, et al. "Histopathological Reactions of a Calcium Phosphate Cement Root Canal Filler," IADR Abstract (1991).

Sanin, et al. "Particle Size Effects on pH and Strength of Calcium Phosphate Cement" IADR Abstract (1991) no month available.

Link, et al. "Composite of Calcium Phosphate Cement and Genetically Engineered Protein Bioadhesive", IADR Abstract (1991) no month available.

Matsuya, et al. "Effects of pH on the Reactions of Tetracalcium Phosphate and Dicalcium Phosphate" IADR Abstract (1991) no month available.

Chow, et al. "X–ray Diffraction and Electron Microscopic Characterization of Calcium Phosphate Cement Setting Reactions" IADR Abstract (1991) no month available.

Sugawara, et al. "An In Vitro Study of Dentin Hypersensitivity Using Calcium Phosphate Cement" Jour. of Japanese Soc. for Dent. Mats & Devices, vol. 8, No. 2, (1988) no month available.

Constantino, et al. "Hydroxyapatite Cement—Basic Chemistry and Histologic Properties" Arch. of Otolaryngology— Head & Neck Surgery, vol.117, pp.379–384 no month available (1991).

Freidman, et al, "Hydroxyapatite Cement — Obliteration and Reconstruction of the Cat Frontal Sinus" Arch. of Otolaryngogogy— Head & Neck Surgery, vol. 117, pp. 385–389, (1991) no month available.

Mirtchi, et al. "Calcium Phosphate Cements: Study of the β–tricalcium phosphate–monocalcium Phosphate System" Biomaterials, vol. 10, pp. 475–480 (1989) no month available.

Mirtchi, et al. "Calcium Phosphate Cements: Action of Setting regulars On The Properties of the β–tricalcium Phosphate–monocalcium Phosphate System" Biomaterials, vol. 10, pp. 3634–3638 (1989) no month available.

Mirtchi, et al. "Calcium Phosphate Cements: Study of the β–tricalcium Phosphate dicalcium Phosphate–calcite Cements" Biomaterials, vol. 11, pp. 83–88 (1990) no month available.

Mirtchi, et al. "Calcium Phosphate Cements: Effect of Fluorides On The Setting and Hardening of β–tricalcium Phosphate–dicalcium Phosphate–calcite Cements" Biomaterials, vol. 12, pp. 505–510 (1991) no month available.

Fulmer, et al. "Effects of $Na_2HPO_4$ and $NaH_2PO_4$ on Hydroxyapatite Formation" J. Biomed. Mat. Res. vol. 27, pp. 1095–1102 (1993) no month available.

Ishikawa, et al., "The Hydrolysis of Anhydrous Dicalcium Phosphate Into Hydroxyapatite," J. Dent. Res., vol. 72, No. 2 pp. 474–480 (1993) no month available.

Sugawara, et al. "In Vitro Evaluation Of The Sealing Ability of A Calcium HPhosphate Cement When Used as A Root Canal Sealer–Filler" J. of End. vol. 16 No. 4, pp. 162–165 (1990) no month available.

Shindo, et al. "Facial Skeletal Augmentation Using Hydroxyapatite Cement" Arch. of Otolaryngology — Head & Neck Surgery, vol. 119, pp. 185–190 (1993) no month available.

Constantino, et al. "Experimental Hydroxyapatite Cement Cranioplasty" Plastic and Reconstructive Surgery vol. 90 No. 2, pp. 174–185 (1992) no month available.

SELF-SETTING CALCIUM PHOSPHATE CEMENTS AND METHODS FOR PREPARING AND USING THEM

This invention was made in the course of research partially supported by a government grant from the National Institute of Dental Research (Grant No. DE 05030). The U.S. government has certain rights in the invention.

BACKGROUND OF THE INVENTION

1. Field of the Invention

This invention relates to calcium phosphate compositions, including cements and pastes, and to methods for making and using them. In its preferred form, the invention relates to methods for making hydroxyapatite forming cements and pastes without the necessity for employing tetracalcium phosphate as a precursor.

2. Description of Related Art

In the area of dental cements, the prior art includes a number of compounds. Some such cements, however, irritate the pulp and are unsuitable for applications where the cement must come in contact with exposed pulp. Guide to Dental Materials and Devices, 7th Ed. (ADA 1974) p. 49. One solution to this problem is a cement made of materials similar in composition to tooth and bone mineral, since this would not irritate the living tissue. It has been known for some time that hydroxyapatite materials have the basic properties of human bones and teeth.

The use of $\beta$-$Ca_5(PO_4)_2$ was suggested for pulp capping in Driskell et al., "Development of Ceramic and Ceramic Composite Devices for Maxillofacial Application", J. Biomed. Mat. Res. 6:345–361 (1972); and the use of $Ca_4(PO_4)_2O$ was suggested by Brown and Chow in IADR Abstract No. 120, J. Dent. Res. 54:74 (1975), as a possible pulp capping agent. As described in the latter, $Ca_4(PO_4)_2O$ hydrolyzes to hydroxyapatite. Such single calcium phosphate cements are incapable of setting to a hard consistency, however, without an additional source of calcium.

Though U.S. Pat. No. 3,913,229 (Driskell et al.) discloses putty-like pastes containing $\alpha$-$Ca_3(PO_4)_2$, $\beta$-$Ca_3(PO_4)_2$, $CaHPO_4$ and mixtures thereof as pulp capping, root canal, and tooth replanting materials, it is believed that none of these pastes hardens into a cement.

Experience with calcium-based implants for the replacement of skeletal tissue has also existed for many years. Most of these implants have been in the form of prefabricated, sintered hydroxyapatite in either granule or block forms. These preparations have several drawbacks, including a limited ability to conform to skeletal defects, particularly in the case of blocks; inadequate structural integrity of granules (which do not bond together), and difficulty in modeling the implant to the shape of missing skeletal tissue with both blocks and granules. The block form of hydroxyapatite provides structural support, but among other complications, must be held in place by mechanical means, which greatly limits its use and its cosmetic results; and it is very difficult to saw a shape such that it fits the patient's individual defect. The granular form produces cosmetically better results, but has a very limited structural stability and is difficult to contain during and after a surgical procedure. In general, all of these products are ceramics, produced by high temperature sintering, and are not individually crystalline, but rather have their crystal boundaries fused together. These ceramic-type materials are in general functionally biologically non-absorbable (having an absorption rate generally not exceeding on the order of 1% per year).

A porous, non-resorbable material based on coral allows intergrowth with bone, but ultimately becomes only approximately 20% bone with the remaining 80% subsisting as scar tissue. HA RESORB made by Osteogen is a form of absorbable hydroxyapatite, but is not a cement. It is granular and not adhesive. HA RESORB is loosely rather than adhesively packed into place. For large uses, it is replaced by bone too quickly. In the dental materials market, HAPSET is a composition of calcium phosphate granules and cementable plaster of Paris (calcium sulfate). This material is not truly a hydroxyapatite and contains too much calcium sulfate for most biological uses. The calcium sulfate component of such a composition is resorbable, but not the calcium phosphate granules.

In sum, the commercially available hydroxyapatite materials are in general not resorbable with accompanying replacement by bone, and are not self-setting (self-hardening) cements.

The patent literature, does, however, describe at least one class of calcium phosphate cement compositions which are precursors for the formation of hydroxyapatite and are biologically compatible, and have two unique properties' that are not attainable in other calcium phosphate biomaterials: (1) self-hardening to form a mass with sufficient strength for many medical and dental applications, and (2) when implanted in bone, the cement resorbs slowly and is completely replaced by new bone formation with no loss in the volume or integrity of the tissue that receives the implant. See U.S. Pat. Nos. Re. 33,221 and Re. 33,161 to Brown and Chow, which teach preparation of calcium phosphate remineralization compositions and of a finely crystalline, non-ceramic, gradually resorbable hydroxyapatite cement based on the same calcium phosphate composition.

A virtually identical calcium phosphate system which consists of tetracalcium phosphate (TTCP) and monocalcium phosphate (MCP) or its monohydrate form (MCPM) was described by Constantz et al. (U.S. Pat. Nos. 5,053,212 and 5,129,905). This cement system is believed to involve conversion of the MCP to dicalcium phosphate which reacts with TTCP and forms hydroxyapatite (HA), the major mineral component of teeth and bone, as the end product.

Constantz et al. U.S. Pat. Nos. 4,880,610 and 5,047,031 describe another cement system that consists of a mixture of solid phosphoric acid crystals, calcium carbonate, and calcium hydroxide as the cement powder and a 7.4 mol/L NaOH solution (4.5 g NaOH in 15 mL of water) as the cement liquid. Data on the physical and chemical properties (compressive strength, hardening time, nature of end product, pH of the cement fluid, heat of mixing etc.) of this cement have not been located in the patent or scientific literature.

The major components of the calcium phosphate remineralizing slurries, pastes and cements taught in U.S. Pat. Nos. Re. 33,221 and Re. 33,161 are preferably tetracalcium phosphate ($Ca_4(PO_4)_2O$), and at least one other sparingly soluble calcium phosphate, preferably dicalcium phosphate anhydrous ($CaHPO_4$), or dicalcium phosphate dihydrate ($CaHPO_4 \cdot 2H_2O$). These react in an aqueous environment to form hydroxyapatite, the principal mineral in teeth and bones, as the final product. Because of the apatitic nature of the set cement, it is highly compatible with soft and hard tissues. This material, if applied intraoperatively as a paste, subsequently sets to a structurally stable implant composed of microporous hydroxyapatite.

SUMMARY OF THE INVENTION

The materials of Brown and Chow U.S. Pat. Nos. Re. 33,221 and Re. 33,161, while highly useful, are relatively expensive because of the cost of tetracalcium phosphate.

Applicants have discovered that use of tetracalcium phosphate may be avoided in the preparation of the calcium phosphate cement composition, while still yielding a product which self-sets to hydroxyapatite, provided: (1) a high phosphate concentration is maintained in the precursor slurry solution, and/or (2) the pH is substantially elevated above neutral. In particular, applicants have discovered that the use of a calcium phosphate precursor slurry without TTCP, which has a phosphate concentration in the solution at or above about 0.2 mol/L and/or a pH in the range of from about 12.5 to about 14 results in a cement which sets reliably and quickly to HA without the use of tetracalcium phosphate in the precursor mixture. Applicants have also discovered that the rate of conversion to HA is unchanged for calcium phosphate cements prepared by this method and setting times are improved. The setting rate can be adjusted for various end uses, and may be quite rapid if desired. The inventive hydroxyapatite cement is believed to be both biocompatible and resorbable (biodegradable) with bone replacement when in contact with living bone.

The invention includes a method for preparing calcium phosphate cement compositions, which self-harden substantially to hydroxyapatite at ambient temperature when in contact with an aqueous medium, comprising combining one or more sparingly soluble calcium phosphates other than tetracalcium phosphate with an aqueous phase having sufficient dissolved phosphate salt to yield a solution mixture with phosphate concentration equal to or greater than about 0.2 mol/L. The invention further includes a method for preparing calcium phosphate cement compositions, which self-harden substantially to hydroxyapatite at ambient temperature when in contact with an aqueous medium, comprising combining one or more sparingly soluble calcium phosphates other than tetracalcium phosphate with an aqueous phase such that the pH of the solution following combination is initially in the range of about 12.5 to about 14. Alternatively, the inventive method may involve utilization of both these sets of conditions simultaneously.

The invention further contemplates the improved calcium phosphate cement mixtures prepared by this method, the cement component(s) provided to the user in a premanufactured kit or delivery device, the methods of using the improved cement, and the biological implants made from the cement. A self-hardening industrial cement is also contemplated.

The techniques previously commercially available for repair of cranio- and maxillofacial defects, periodontal defects, bone fractures and other dental and orthopedic defects which could not be successfully self-healed relied heavily on the use of metallic and ceramic inserts and prostheses which might remain indefinitely as foreign objects in the body of a human or veterinary patient. As such, these prior art techniques suffered from a host of related problems, including possible rejection, sites for infection, structural failure, injury to neighboring tissue and the like. Metals are difficult to shape and are hampered by problems such as infection and corrosion. Polymers such as silicone, PROPLAST, or methyl-methacrylate are encapsulated by scar tissue resulting in significant rates of implant infection and/or extrusion. Biologic materials, such as autogenous bone grafts, may cause donor site morbidity, may suffer from significant post-implantation resorption, and are difficult to accurately conform to skeletal defects. U.S. Pat. Nos. Re. 33,221 and Re. 33,161 and pending application Ser. No. 08/030,709 offer the alternative of a hydroxyapatite-forming calcium phosphate cement which is biocompatible and which when implanted in contact with living bone, is largely if not completely replaced by new bone formation, with no significant loss in the volume or integrity of the tissue that receives the implant. The above-cited patents to Brown and Chow teach the preparation of bioresorbable cements preferably from combinations of tetracalcium phosphate ($Ca_4(PO_4)_2O$) and another sparingly soluble calcium phosphate compound, preferably dicalcium phosphate or dicalcium phosphate dihydrate. The above-cited application, Ser. No. 08/030,709 teaches the preparation of calcium deficient HA from specially prepared and stored tetracalcium phosphate and another sparingly soluble calcium phosphate compound.

The inventive method described and claimed herein results in cements which are characterized by many important advantages as compared with traditional hydroxyapatite materials, and which are significantly less expensive than those of Brown and Chow and of Chow and Takagi, cited above.

An object and advantage of the present invention is the provision of a method for preparing a self-setting calcium phosphate cement which results in particularly rapid setting of the cement.

A further object and advantage of the invention is the provision of a method for making a calcium phosphate cement which employs less expensive starting materials than prior art cements of comparable properties.

Further objects and advantages of the invention include the cement mixtures prepared by the inventive method, the methods of using the cements, and the products made from them embodying the characteristics set forth above.

Additional advantageous attributes of the inventive cement include the following:

The cement is easy to use and can be readily modeled to accurately reconstruct bony cavities and missing bone and to recreate contour defects of relatively non-stress bearing skeletal bone.

The cement or paste consistency enables the hydroxyapatite to conform exactly to the contours of a defect. The cement can be applied to a defect, e.g., with a spatula, can be molded and sculpted, and will hold its shape satisfactorily until set.

The inventive cement sets at ambient temperature, e.g., room or body temperature, unlike the ceramic-type calcium phosphate cements which must be sintered at high temperature in a process that fuses individual hydroxyapatite crystals to each other. The cement setting reaction for the inventive material is isothermic (negligible heat is generated) and thus does not result in heat-generated necrosis of any of the neighboring tissue.

The inventive cement can be easily sculpted in vivo (intraoperatively) even after setting. When applied to clean, non-infected bone, the cement adheres to the bone, thereby greatly increasing its possible applications. Additionally, the inventive cements of the present invention are especially useful in in vitro applications, including the creation of implants. In general, the cement can be adapted to many applications.

The instant cement represents a highly biocompatible tissue substitute precursor or synthetic implant material for skeletal reconstruction. This biocompatibility stems from the fact that calcium phosphate exists in bone in the form of hydroxyapatite, and it is therefore a chemically natural material. Basically, the inventive cement is regarded by the body as a native material; the elevated pH which characterizes certain forms of the cement rapidly diminishes to neutral and therefore presents little threat of injury to the surrounding tissue.

DESCRIPTION OF THE PREFERRED EMBODIMENTS

The complete disclosures of U.S. Pat. Nos. Re. 33,221 and Re. 33,161 and pending application Ser. No. 08/030,709 are expressly incorporated herein by reference.

The inventive hydroxyapatite cement is an alternative to the self-setting cement of calcium phosphate compounds developed by Brown and Chow and referenced above. The preferred major components of the calcium phosphate cement of Brown and Chow are tetracalcium phosphate (TTCP) and dicalcium phosphate anhydrous (DCPA) or dicalcium phosphate dihydrate (DCPD). These react in an aqueous environment to form hydroxyapatite (HA), the principal mineral component of teeth and bones, as the final product.

The chemical reaction that occurs during the setting of the TTCP-DCPA (or TTCP-DCPD) cement described in Brown and Chow (Re. 33,161 and 33,221) can be represented by the following equation:

$$Ca_4(PO_4)_2O + CaHPO_4[.2H_2O] \longrightarrow Ca_5(PO_4)_3OH + [2H_2O] \quad (1)$$

TTCP　　　　　DCPA [DCPD]　　　HA

As described later, the choice of TTCP and DCPA (DCPD) as the cement ingredients is important because the solubilities of TTCP and DCPA are such that the cement fluid, which is approximately saturated with respect to both salts, would have a slightly above neutral pH (about 7.5 to 8.5) and sufficiently high calcium (Ca) and phosphate (P) concentrations so that the solution is substantially supersaturated with respect to HA. Rapid HA formation and concomitant dissolution of both cement ingredients, TTCP and DCPA, lead to the hardening of the cement ordinarily within 30 minutes or less.

Figure 1A:
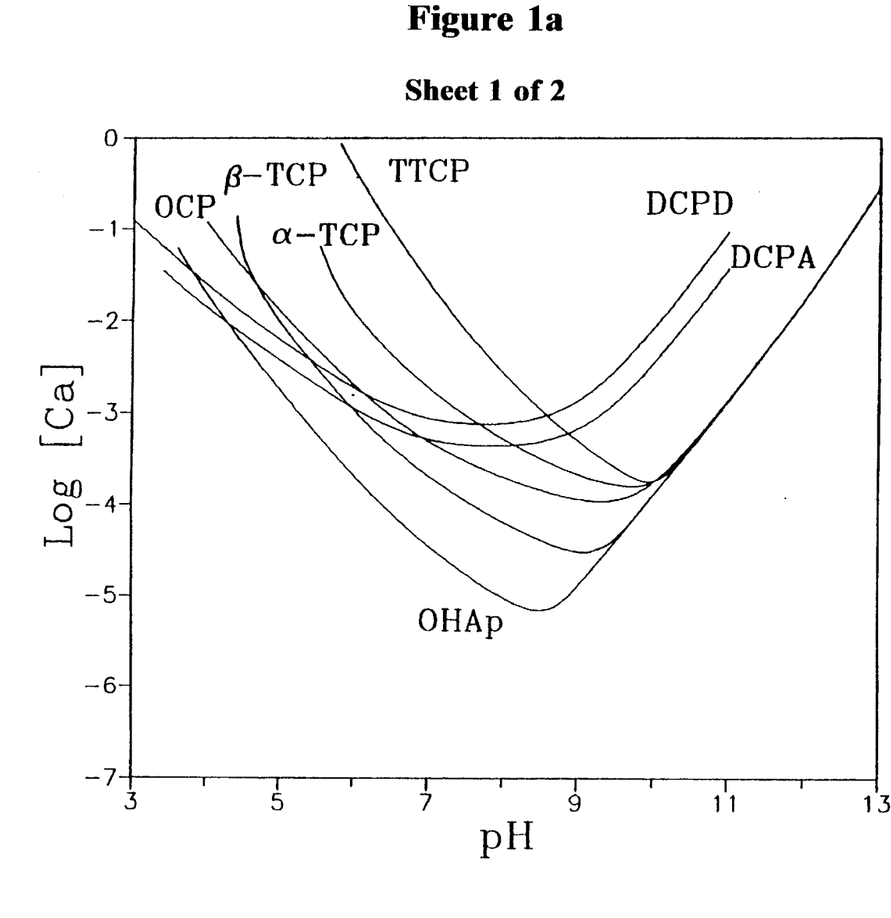
FIGS. 1a and 1b show the solubility phase diagram of the 3-component system, $Ca(OH)_2$-$H_3PO_4$-$H_2O$, in which both the solid phase and the saturated solution contain only those ions or non-charged species that are derived from the three components, $Ca(OH)_2$, $H_3PO_4$ and $H_2O$.
Figure 1B:
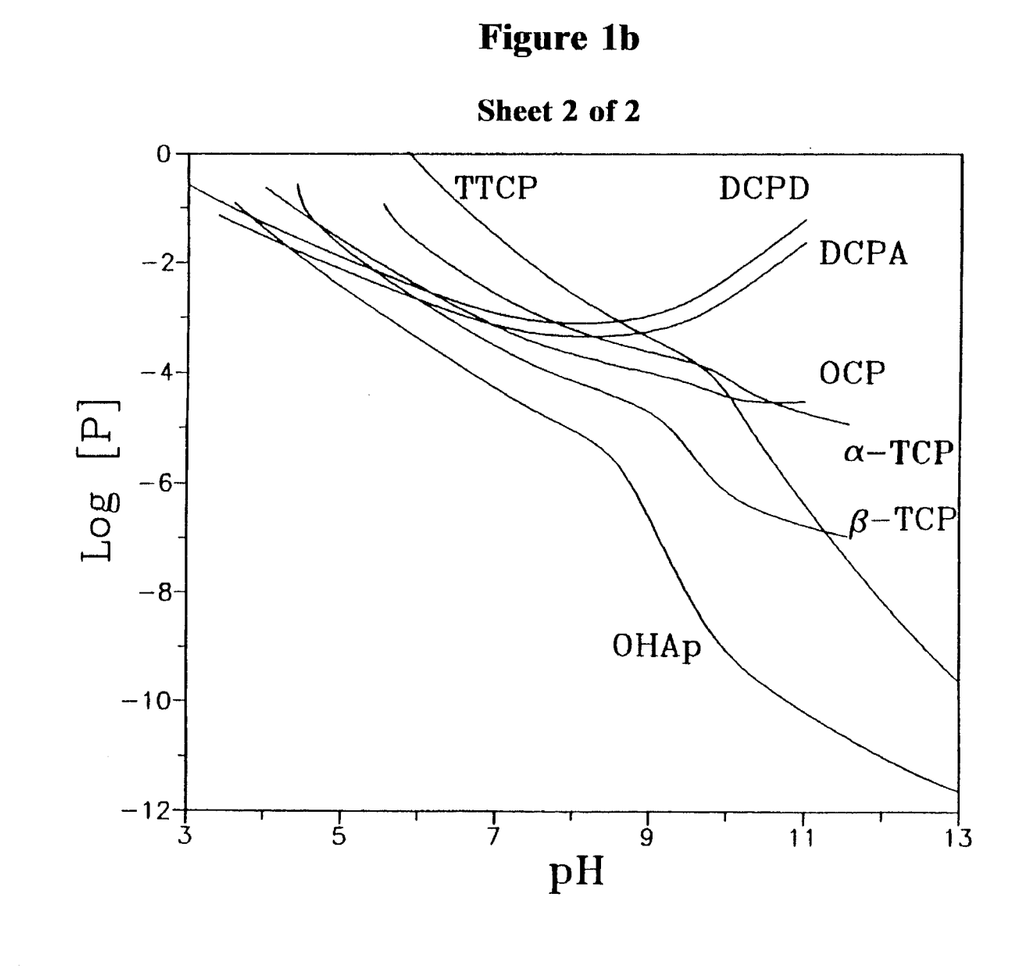

FIGS. 1a and 1b show the solubility phase diagram of the three-component system, $Ca(OH)_2$-$H_3PO_4$-$H_2O$, in which both the solid phase and the saturated solution contain only those ions or non-charged species that are derived from the three components, $Ca(OH)_2$, $H_3PO_4$, and $H_2O$. Each curve, or solubility isotherm, in the diagram represents the composition (in terms of the pH and calcium concentration in FIG. 1a and the pH and phosphate concentration in FIG. 1b) of a series of solutions that are all saturated with respect to a given salt. A calcium phosphate salt that has a solubility isotherm that lies below that of another salt is less soluble (and more stable) than the other salt. It can be seen in the figures that among all calcium phosphate salts, HA is the least soluble in a wide range of solution pH's, ranging approximately from 4.5 to 14. Thus, within this pH range, any other calcium phosphate or mixture of calcium phosphates has the tendency to dissolve and reprecipitate as HA. However, in general the rate of HA formation is very slow such that a slurry of DCPD, DCPA, octacalcium phosphate (OCP), amorphous calcium phosphate (ACP), α-tricalcium phosphate (α-TCP), β-tricalcium phosphate (β-TCP), or a mixture of these salts does not produce a setting cement or act as an effective remineralizing agent.

It has now been discovered that HA formation in calcium phosphate slurries can be greatly accelerated by one or both of the following factors: (1) a high phosphate concentration in the slurry solution, and (2) a high degree of supersaturation with respect to HA produced by raising the solution pH to a level where most of the phosphate is in the form of $PO_4^{3-}$ and little phosphate is in the form of $H_3PO_4$ or $H_2PO_4^-$.

It is believed that the key to the inventive cement system is to provide effective means to accelerate the HA formation in the slurry systems that do not contain TTCP. This can be achieved by producing and maintaining a high phosphate concentration (e.g., 0.2 mol/L or higher), a high degree of supersaturation with respect to HA by raising the solution pH to about 12.5 or above, or both. It is noted that in all cases, the pH of the slurry must be in the range of approximately 4.5 to 14, the range in which HA is the most stable phase. Once this is achieved, rapid HA formation and subsequent cementation can occur in practically any calcium phosphate slurries. Described below are approaches to attain high phosphate concentration and high degree of HA supersaturation in the slurry solutions.

In one embodiment, the invention involves producing and maintaining a high phosphate concentration in the calcium phosphate slurry solution. Contrary to what appears to be the most obvious method to achieve the goal, adding phosphoric acid to a calcium phosphate slurry is not the method of choice to increase the phosphate concentration to 0.2 mol/L or higher. This is because as long as the slurry solution remains as a three-component system, $Ca(OH)_2$-$H_3PO_4$-$H_2O$, the phosphate concentration is limited by the solubility isotherms of the solid that is in contact with the solution (FIG. 1b). Thus, after adding 0.2 mol/L of phosphoric acid, the pH of the slurry would drop to significantly below 4.5 initially. As the calcium phosphate crystals dissolve and pH increases, the phosphate concentration would drop to below 0.1 mol/L as the pH increases to 4.5 (FIG. 1b). An effective way to increase the phosphate concentration is to add a non-calcium-containing salt of phosphoric acid that is sufficiently soluble, e.g., $Na_3PO_4$, $Na_2HPO_4$, or $NaH_2PO_4$. Salts of other cations such as $K^+$, $NH_4^+$, etc., would work equally well provided that the cations do not form strong complexes with phosphate to the point of making phosphate unavailable for HA precipitation.

The reason why a high phosphate concentration can be maintained by adding an appropriate amount of sodium phosphate salt is explained as follows. In the example where the pH is between 7.2 and 12.7, since the solution would always have a $Na^+$ concentration of 0.4 mol/L (regardless of the calcium phosphate dissolution and precipitation reactions that may occur), the total anion concentration in the solution must be such that the anions can provide sufficient negative charges to balance the positive charges of the $Na^+$ ions. Since $OH^-$ and phosphate ions are the only anions present in the solution, and since $OH^-$ concentration would be only 0.01 mol/L even at pH of 12, most of the negative charges have to be provided by the phosphate ions. Further, because in this pH range the dominant phosphate species is $HPO_4^{2-}$, the total phosphate concentration needed to balance the positive charges of the $Na^+$ ions would be approximately 0.2 mol/L.

A second embodiment of the invention involves increasing the degree of supersaturation with respect to HA by increasing the pH to approximately 12.5 or above. The pH can be increased by adding a strong base, e.g., NaOH, KOH, etc. $Ca(OH)_2$ by itself is insufficient to increase the HA formation significantly, but it needs to be included as a solid component as described later. It is noted that raising the pH to 12.5 or above also increases the solubility of those calcium phosphate salts that have $HPO_4^{2-}$ ions in their structures because at pH above approximately 12.7 the dominant phosphate species is the $PO_4^{3-}$ ion. Thus, for slurries that contain these salts, a high phosphate concentration can also be obtained by increasing the pH of the slurry solution to approximately 12 or above. In contrast, raising the pH would not be effective in increasing the phosphate concentration in slurries that contain ACP, α-TCP, or β-TCP.

Regardless of which embodiment of the invention is used, certain considerations apply to the cement setting reactions.

The formation of HA and dissolution of the more soluble calcium phosphate compounds are responsible for the hardening of the cement. Since all calcium phosphates that will be used in the cement starting ingredients have Ca/P molar ratio below 5/3, the Ca/P ratio of HA, an additional source of calcium is needed to form HA as the dominant cement end product. For example, $Ca(OH)_2$, $CaO$ and $CaCO_3$ can be used for this purpose. To achieve complete conversion to HA, the cement should contain stoichiometric amounts of the calcium phosphate ingredients according to the setting reaction. Given below are some representative reactions:

$$3CaHPO_4 + 2Ca(OH)_2 \rightarrow Ca_5(PO_4)_3OH + 3H_2O \quad (3)$$

$$3CaHPO_4 + 2CaO \rightarrow Ca_5(PO_4)_3OH + H_2O \quad (4)$$

$$3CaHPO_4 + 2CaCO_3 \rightarrow Ca_5(PO_4)_3OH + H_2O + 2CO_2 \quad (5)$$

$$3\alpha\text{-}Ca_5(PO_4)_2 + Ca(OH)_2 \rightarrow 2Ca_5(PO_4)_3OH \quad (6)$$

$$3CaHPO_4 \cdot 2H_2O + 2Ca(OH)_2 \rightarrow Ca_5(PO_4)_3OH + 9H_2O \quad (7)$$

$$3 \text{ amorphous } Ca_3(PO_4)_2 + Ca(OH)_2 \rightarrow Ca_5(PO_4)_3OH \quad (8)$$

EXAMPLES 1–58

Calcium phosphate cements were made using the methods of the present invention as follows:

A calcium phosphate cement powder was prepared by mixing a calcium phosphate salt (substantially free of tetracalcium phosphate) such as DCPA, DCPD, α-TCP or ACP with an additional source of calcium such as $CaCO_3$, $Ca(OH)_2$, or CaO. These calcium components may be mixed as received from vendors or ground to smaller particle size. Table I below provides examples of specifications for particles size of the components.

The calcium phosphate cement of the present invention was made by mixing 0.3 gram of calcium phosphate cement powder with 0.075 mL of an aqueous solution of a non-calcium containing salt of phosphoric acid, with powder to liquid weight ratio (P/L) of about 3, such as 1M $Na_2HPO_4$ (P/L=3), 0.5M $Na_2HPO_4$ (P/L=3), 5M $(NH_4)_2HPO_4$ (P/L= 2.5). 1N NaOH and 4N NaOH solutions were also used to formulate the cement. To allow testing of the setting time and strength of the cement, the mixture was spatulated on a glass slab for 30 sec, and placed in a stainless steel mold (6 mm d×3 mm h). The top and bottom surfaces of the mold were tightly covered with glass plates and the mold was placed in a 100% humidity box kept at 37° for 4 hours. The sample was removed from the mold and placed in a small amount of water for 20 hours. The diametral tensile strength (DTS) was measured with the use of a Universal Testing Machine (United Calibration Corp., Garden Grove, Calif.) at a cross-head speed of 1 mm/min. The results of the settings times and the DTS testing are recorded in Table II.

Powder x-ray diffraction (XRD) measurements were taken of the samples to measure the conversion to HA. The samples were first ground into a fine powder form by hand grinding with the use of a mortar and pestle. Approximately 0.25 grams of sample was placed on the sample holder. A computer-controlled powder x-ray diffractometer (Rigaku, Danvers, Mass.) with CuKα radiation generated under the conditions of 40 kv and 25 mA was used to obtain the XRD patterns. Data were collected in the 2 θ scanning mode using a step width of 0.01° and count time of 2 sec.

TABLE I

Specification of Ingredients

| Code | Description | Median particle size (μm) |
|---|---|---|
| DCPA | Dicalcium phosphate anhydrous (JT Baker, Inc.) ($CaHPO_4$) | 11.9 |
| DCPA (g) | DCPA ground in 95% ethanol in a planetary mill for 24 h | 0.65 |
| $Ca(OH)_2$ | Calcium hydroxide (Fisher Scientific Co.) ($Ca(OH)_2$) | 4.5 |
| $Ca(OH)_2$ (g) | $Ca(OH)_2$ ground in cyclohexane for 6 h | 1.36 |
| CaO | Calcium oxide (CERAC/PURE, Inc.) (CaO) | 5.77 |
| $CaCO_3$ | Calcium carbonate (JT Baker) ($CaCO_3$) | 12.4 |
| $CaCO_3$ (g) | $CaCO_3$ ground in cyclohexane for 16 h | 2.55 |
| α-TCP | α-tricalcium phosphate (α-$Ca_3(PO_4)_2$) | 12.5 |
| α-TCP (g) | α-TCP ground in cyclohexane for 22 h | 2.91 |
| ACP | Amorphous calcium phosphate ($Ca_3(PO_4)_2$) | |
| DCPD | Dicalcium phosphate dihydrate (prepared in our laboratory) ($CaHPO_4 \cdot 2H_2O$) | 7.64 |
| DCPD (g) | DCPD ground in 95% ethanol for 24 h | 0.63 |

TABLE II

Properties of Cement and Comparative Formulations

| Example | Solid Components | Liquid | P/L | Setting time | DTS (MPa) | Conversion to HA |
|---|---|---|---|---|---|---|
| 1 | DCPA + $Ca(OH)_2$ DCPA (g) + $Ca(OH)_2$ | 0.5M $Na_2HPO_4$ | 3 | 7 | 3.9 | |
| 2 | DCPA (g) + $Ca(OH)_2$ | 1M $Na_2HPO_4$ | 3 | 5 | 2.4 | |
| 3 | DCPA (g) + $Ca(OH)_2$ | 1M $Na_2HPO_4$ | 2.5 | 5 | 3.7 ± .2 | ~100% HA |
| 4 | DCPA (g) + $Ca(OH)_2$ | 5M $(NH_4)_2HPO_4$ | 2.5 | 5 | 2.5 ± .2 | 90% + DCPA |

TABLE II-continued

Properties of Cement and Comparative Formulations

| Example | Solid Components | Liquid | P/L | Setting time | DTS (MPa) | Conversion to HA |
|---|---|---|---|---|---|---|
| 5 | DCPA (g) + Ca(OH)$_2$ | 1N NAOH | 2.5 | 12 | 2.6 ± .8 | ~100% HA |
| 6 | DCPA (g) + Ca(OH)$_2$ | 4N NAOH | 3 | 10 | 3.9 | |
| 7 | DCPA (g) + Ca(OH)$_2$ | 4N NAOH | 2.5 | 5 | 1.5 | |
| 8 | DCPA + Ca(OH)$_2$ | 1M Na$_2$HPO$_4$ | 2.5 | 8 | 1.2 ± .2 | HA + DCPA |
| 9 | DCPA + Ca(OH)$_2$ | 5M (NH$_4$)$_2$HPO$_4$ | 3 | 11 | .72 | |
| 10 | DCPA + Ca(OH)$_2$ | 4N NAOH | 3 | 12 | 2.3 | 100% HA |
| 11 | DCPA (g) + Ca(OH)$_2$(g) | 1M Na$_2$HPO$_4$ | 2.5 | 10 | 3.9 ± .2 | 95% HA |
| 12 | DCPA (g) + CA(OH)$_2$(g) | 1N NaOH | 2.5 | 40 | 1.6 ± .3 | 95% HA |
| 13 | DCPA (g) + CA(OH)$_2$(g) | 25 mM H$_3$PO$_4$ | 2.5 | 30 | | |
| | DCPA + CaO | | | | | |
| 14 | DCPA + CaO | 1M Na$_2$HPO$_4$ | 3 | 10 | 1.2 ± 0.2 | |
| 15 | DCPA + CaO | 1N NaOH | 3 | 22 | | |
| 16 | DCPA + CaO | 25 mM H$_3$PO$_4$ | 3 | no setting | | |
| 17 | DCPA (g) + CaO | 1M Na$_2$HPO$_4$ | 2.5 | 10 | 2.0 ± .03 | 90% HA |
| 18 | DCPA (g) + CaO | 1N NAOH | 2.5 | 10 | 1.7 ± .5 | 70% HA |
| 19 | DCPA (g) + CaO | 25 mM H$_3$PO$_4$ | 2.5 | 30 | | |
| | DCPA + CaCO$_3$ | | | | | |
| 20 | DCPA (g) + CaCO$_3$ | 1M Na$_2$HPO$_4$ | 2.5 | >2 h | 1.1 | 10% HA |
| 21 | DCPA (g) + CaCO$_3$ | 5M (NH$_4$)$_2$HPO$_4$ | 4 | >2 h | 1.6 | |
| 22 | DCPA (g) + CaCO$_3$ (g) | 1M Na$_2$HPO$_4$ | 3 | 20 | 1.5 ± .2 | 99% HA |
| 23 | DCPA (g) + CaCO$_3$ (g) | 1N NaOH | 3 | 60 | 1.0 ± .3 | 90% HA |
| 24 | DCPA (g) + CaCO$_3$ (g) | 25 mM H$_3$PO$_4$ | 3 | no setting | | |
| | α-TCP and CaO | | | | | |
| 25 | α-TCP + CaO | 1M Na$_2$HPO$_4$ | 2.5 | 2h | 60% | |
| 26 | α-TCP + CaO | 1N NaOH | 2.5 | 2 h | 0.8 | 90% |
| 27 | α-TCP + CaO | 5M (NH$_4$)$_2$HPO$_4$ | 2.5 | 2 h | 1.7 | 95% |
| 28 | α-TCP + CaO | 2M Citric acid | 2.5 | 22 | 1.6 | |
| 29 | α-TCP + CaO | 1N HCl | 3 | no setting | | |
| 30 | α-TCP (g) + CaO | 1N NaOH | 3 | 10 | 0.9 ± 0.3 | |
| 31 | α-TCP (g) + CaO | 25 mM H$_3$PO$_4$ | 3 | no setting | | |
| 32 | α-TCP (g) + CaO | 1M Na$_2$HPO$_4$ | 3 | 20 | 0.9 ± 0.4 | |
| | α-TCP + Ca(OH)$_2$ | | | | | |
| 33 | α-TCP + Ca(OH)$_2$ | 1M Na$_2$HPO$_4$ | 2.5 | no setting | | |
| 34 | α-TCP + Ca(OH)$_2$ | 1N NaOH | 2.5 | no setting | | |
| 35 | α-TCP + Ca(OH)$_2$ | 5M (NH$_4$)$_2$HPO$_4$ | 2.5 | >2 h 6.5 | | |
| 36 | α-TCP (g) + Ca(OH)$_2$ | 1M Na$_2$HPO$_4$ | 3 | 20 | 1.3 ± .2 | 99% |
| 37 | α-TCP (g) + Ca(OH)$_2$ | 1N NaOH | 3 | no setting | | |
| 38 | α-TCP (g) + Ca(OH)$_2$ | 25 mM H$_3$PO$_4$ | 3 | no setting | | |
| 39 | α-TCP + Ca(OH)$_2$ (g) | 1M Na$_2$HPO$_4$ | 3 | 1 day 0.2 | | |
| 40 | α-TCP + Ca(OH)$_2$ (g) | 1N NaOH | 3 | no setting | | |
| 41 | α-TCP + Ca(OH)$_2$ | 1M Na$_2$HPO$_4$ | 3 | 20 | 2.7 ± .2 | 99% |
| 42 | α-TCP(g) + Ca(OH)$_2$(g) | 1N NaOH | 3 | 20 | 1.8 ± .5 | 99% |
| 43 | α-TCP(g) + Ca(OH)$_2$(g) | 25 mM H$_3$PO$_4$ | 3 | no setting | | |
| | α-TCP + CaCO$_3$ | | | | | |
| 44 | α-TCP + CaCO$_3$ | 1M Na$_2$HPO$_4$ | 3 | 1 day 1.4 | | |
| 45 | α-TCP + CaCO$_3$ | 1N NaOH | 3 | no setting | | |
| 46 | α-TCP (g) + CaCO$_3$ | 1M Na$_2$HPO$_4$ | 3 | 20 | 4.8 ± 1.2 | 95% |
| 47 | α-TCP (g) + CaCO$_3$ | 1N NaOH | 3 | 20 | 2.7 ± .7 | 95% |
| 48 | α-TCP (g) + CaCO$_3$ | 25 mM H$_3$PO$_4$ | 3 | no setting | | |
| 49 | α-TCP + CaCO$_3$ (g) | 1M Na$_2$HPO$_4$ | 3 | 1 day | | |
| 50 | α-TCP + CaCO$_3$ (g) | 1N NaOH | 3 | no setting | | |
| 51 | α-TCP(g) + CaCO$_3$(g) | 1M Na$_2$HPO$_4$ | 3 | 20 | 7.5 ± .5 | 99% |
| 52 | α-TCP(g) + CaCO$_3$(g) | 1N NaOH | 3 | 75 | 2.7 ± .6 | 99% |
| 53 | α-TCP(g) + CaCO$_3$(g) | 0.2M Na$_2$HPO$_4$ | 3 | 15 | 3.7 ± 1.3 | |
| | ACP + Ca(OH)$_2$ | | | | | |
| 54 | ACP + Ca(OH)$_2$ | 1M Na$_2$HPO$_3$ | 1.3 | 18 | .14 | |
| 55 | ACP + Ca(OH)$_2$ | 1N NaOH | 1.3 | 25 | −0 | |
| | Three-Component | | | | | |
| 56 | DCPA(g) + Ca(OH)$_2$ + CaCO$_3$ | 1M Na$_2$HPO$_4$ | 2.5 | 12 | 3.9 | HA + CaCO$_3$ |
| | DCPD + Ca(OH)$_2$ | | | | | |
| 57 | DCPD(g) + Ca(OH)$_2$(g) | 1M Na$_2$HPO$_4$ | 3 | 10 | 1.5 ± 0.3 | |
| 58 | DCPD(g) + Ca(OH)$_2$(g) | 1N NaOH | 3 | 21 | 2.0 ± 0.4 | |

Additional data points on DCPD+Ca(OH)$_2$ cement indicate that DCPD is very similar to DCPA in terms of the resulting cement properties. It is believed that OCP setting will generally be slower. β-TCP is considered to be the least desirable calcium phosphate salt to be used in the invention.

While the liquid phase that must be used with the new cements may be less biocompatible for certain clinical applications, and at present the strength of the inventive cement is lower than the best values obtainable for the TTCP-containing calcium phosphate cement, the new calcium phosphate cement is believed highly useful in most applications. The inventive hydroxyapatite cement is sufficiently structurally stable for reconstruction and augmentation of relatively non-stress-bearing bony tissue, although without augmentation, it may not have sufficient shearstrength resistance to function in the reconstruction of stress-bearing bones.

The inventive cement may be supplied to the user in a variety of forms, including as powders or as a powder mixture which is later mixed with the liquid diluent to make a putty; or as a pre-mixed putty which may contain a non-aqueous extender, e.g., glycerin and/or propylene glycol. It may be supplied with or in the instrumentation which is used to introduce the cement into the body, for example, a syringe, percutaneous device, "gun", cannula, biocompatible packet, dentula, reamer, file, or other forms which will be apparent to those of ordinary skill in the art. It is contemplated that the cement, in any of these forms, may be made available to the surgeon, veterinarian or dentist via a kit containing one or more of its key components. The cement is generally provided or employed in a sterilized condition. Sterilization may be accomplished, e.g., by gamma-ray radiation, typically at a dose of 2.5 Mrad.

The inventive cement may be employed in a variety of medical, dental and veterinarian procedures to substitute for missing or defective bone or tooth tissue. For example, it is contemplated that the cements of the present invention may be used in place of any of the cements known in the prior art as: (1) cavity bases and liners to protect the pulp, (ii) materials for capping exposed pulps, (iii) materials to replace or promote regeneration of bone mineral lost due to periodontal disease, (iv) direct filling materials (may be temporary) that have physical properties similar to enamel and are adhesive to enamel and dentin, (v) a cement to build up alveolar ridges in edentulous patients, (vi) an endodontic filling material for root canals, (vii) a material to cement retention pins, (viii) a material for filling sockets after a tooth extraction, (ix) a replacement of bone that has been removed surgically or lost due to trauma, (x) a cement for implanting or replanting teeth, (xi) a luting cement in dentistry and orthopedic surgery, (xii) an investment mold material, (xiii) a material which will promote bone mineral in its vicinity, (xiv) a remineralizing polish for use in place of pumice, and (xv) a root cement for remincralizing and desensitizing of exposed root surfaces, (xvi) a cement for orthopedic prostheses, (xvii) a tooth implant, (xviii) a device for percutaneous passage of tubes, wires and other medical instruments through the skin, (xxix) a replacement material for bone loss due to abscess and (xxx) a self-setting cement for binding non-self-setting calcium phosphate biomaterials such as porous or non-porous HA and $\beta$-tricalcium phosphate. Reconstruction of cleft palate and other congenital skeletal defects is contemplated with use of the inventive cement, as are other forms of reconstructive and cosmetic surgery.

Various additives may be included in the inventive cements, slurries and pastes to adjust their properties and the properties of the hydroxyapatite products made from them. For example, proteins, medicaments, supporting or strengthening filler materials, crystal growth adjusters, viscosity modifiers, pore forming agents, osteoinductive factors such as demineralized bone, bone morphogenic proteins and other additives may be incorporated without departing from the scope of this invention. The referenced filler materials may include non-toxic biocompatible natural or synthetic polymers, non-toxic biocompatible metals such as titanium mesh, or other non-toxic biocompatible organic and inorganic materials. These fillers can be in the form of granules, fibers, rods, sheets or grids. These filler materials enhance the strength of the cement.

In addition, the referenced pore forming agents create pores or channels sufficiently large to cause vascularization of tissue which infiltrates the cement once placed in the body. Such pore forming agents are preferably substantially insoluble in the cement and can be removed by either resorbsion into body tissue, dissolution in physiological fluids, dissolution in solvents or heating after the cement has hardened. The pore forming agents may include sugar, sodium bicarbonate and phosphate salts. The phosphate salts are effective pore forming agents because the use of concentrated phosphate solutions in the cement makes them relatively insoluble in the cement. A particularly useful phosphate salt is disodium phosphate.

An additive of particular significance in dental applications is fluoride containing compounds. When fluoride salts such as $NaF$, $CaF_2$, $SnF_2$, $Na_2PO_3F$ or $Na_2SiF_6$ are added in sufficient quantity they increase the rate of formation of HA and fluorapatite. Preferably, the calcium phosphate cements will have a fluoride content of about 3.8%.

Other especially useful additives are seed crystals of HA or fluorapatite and gelling agents. Adding a sufficient quantity of crystals of HA or fluorapatite to the cement increases the rate of conversion to HA and thus reduces the setting time of the cement. Gelling agents such as hydroxypropyl methylcellulose, carboxyl methylcellulose, starch, proteoglycans and glycoproteins have the effect of causing more rapid hardening of the cement.

The novel implants thus prepared are also contemplated as part of the present invention. Where such implants contact living bone tissue, it is believed that the lack of fusion of the hydroxyapatite crystallites resulting from the setting reaction of the inventive cement will allow osteoclasts to slowly resorb the implants over time.

While the primary benefits of the present invention are believed to relate to dental, medical and veterinary applications, it is also contemplated that the techniques may be employed in conjunction with an industrial hydroxyapatite cement, for example, to repair damage, e.g., from corrosion, to marble and other stone articles.

It should be understood that the foregoing disclosure emphasizes certain specific embodiments of the invention and that all modifications or alternatives equivalent thereto are within the spirit or scope of the invention as set forth in the appended claims.

What is claimed is:

1. A method for making a calcium phosphate cement which self-sets to hydroxyapatite as the predominant product at ambient temperatures comprising (1) preparing an aqueous solution of phosphate having a concentration of about 0.2 mol/L or above and adjusting the pH of the solution with base to about 12.5 or above, and (2) combining the aqueous solution with a calcium phosphate salt having a calcium to phosphorus molar ratio of less than 5 to 3 which is other than tetracalcium phosphate, and with an additional source of calcium selected from the group consisting of calcium carbonate, calcium oxide and calcium hydroxide, in the absence of solid crystalline phosphoric acid.

2. A method for making a calcium phosphate cement which self-sets to hydroxyapatite as the predominant product at ambient temperatures comprising preparing a mixture of a calcium phosphate salt having a calcium to phosphorus molar ratio of less than 5 to 3 which is other than tetracalcium phosphate, an additional source of calcium selected from the group consisting of calcium carbonate, calcium oxide and calcium hydroxide, water, a non-calcium containing phosphate salt at a concentration of about 0.2 mols/L or above and base effective to adjust the pH to about 12.5 or above, in the absence of solid crystalline phosphoric acid.

3. A method for making a calcium phosphate cement which self-sets to hydroxyapatite as the predominant product at ambient temperatures comprising combining a calcium phosphate salt consisting essentially of dicalcium phosphate or dicalcium phosphate dihydrate, with an additional source of calcium selected from the group consisting of calcium carbonate, calcium oxide and calcium hydroxide and an aqueous solution adjusted with base to maintain a pH of about 12.5 or above.

4. A method for making a calcium phosphate cement which self-sets to hydroxyapatite as the predominant product at ambient temperatures comprising preparing a mixture of a calcium phosphate salt consisting essentially of dicalcium phosphate or dicalcium phosphate dihydrate, an additional source of calcium selected from the group consisting of calcium carbonate, calcium oxide and calcium hydroxide, water and base effective to maintain a pH of about 12.5 or above.

5. A method for making a calcium phosphate cement which self-sets to hydroxyapatite as the predominant product at ambient temperatures comprising (1) preparing an aqueous solution of a non-calcium containing salt of phosphoric acid having a concentration of phosphate of about 0.2 mols/L or above, and (2) combining the aqueous solution with a calcium phosphate salt having a calcium to phosphorus molar ratio of less than 5 to 3 which is other than tetracalcium phosphate, and with an additional source of calcium selected from the group consisting of calcium carbonate, calcium oxide and calcium hydroxide, in the absence of solid crystalline phosphoric acid.

6. A method for making a calcium phosphate cement which self-sets to hydroxyapatite as the predominant product at ambient temperatures comprising preparing a mixture of a calcium phosphate salt having a calcium to phosphorus molar ratio of less than 5 to 3 which is other than tetracalcium phosphate, an additional source of calcium selected from the group consisting of calcium carbonate, calcium oxide and calcium hydroxide, water and a non-calcium containing salt of phosphoric acid at a concentration of phosphate of about 0.2 mols/L or above, in the absence of solid crystalline phosphoric acid.

7. A calcium phosphate composition which self-hardens to hydroxyapatite as the predominant product at ambient temperature comprising a calcium phosphate salt having a calcium to phosphorus molar ratio of less than 5 to 3 which is other than tetracalcium phosphate, an additional source of calcium selected from the group consisting of calcium carbonate, calcium oxide and calcium hydroxide, and an aqueous phosphate solution of pH about 12.5 or above with phosphate concentration of about 0.2 mol/L or above, in the absence of solid crystalline phosphoric acid.

8. A calcium phosphate composition which self-hardens to hydroxyapatite as the predominant product at ambient temperature comprising a calcium phosphate salt having a calcium to phosphorus molar ratio of less than 5 to 3 which is other than tetracalcium phosphate, an additional source of calcium selected from the group consisting of calcium carbonate, calcium oxide and calcium hydroxide, water, phosphate salt at a concentration of about 0.2 mols/L or above and base effective to maintain the pH at 12.5 or above, in the absence of solid crystalline phosphoric acid.

9. A calcium phosphate composition, which self-hardens to hydroxyapatite as the predominant product at ambient temperature, comprising a calcium phosphate consisting essentially of dicalcium phosphate or dicalcium phosphate dihydrate, an additional source of calcium selected from the group consisting of calcium carbonate, calcium oxide and calcium hydroxide and an aqueous solution having a pH of about 12.5 or above.

10. A calcium phosphate composition, which self-hardens to hydroxyapatite as the predominant product at ambient temperature, comprising a calcium phosphate consisting essentially of elicalcium phosphate or dicalcium phosphate dihidrate, an additional source of calcium selected from the group consisting of calcium carbonate calcium oxide and calcium hydroxide, water and a base effective to adjust the pH to about 12.5 or above.

11. A calcium phosphate composition, which self-hardens to hydroxyapatite as the predominant product at ambient temperature, comprising a calcium phosphate salt having a calcium to phosphorus molar ratio of less than 5 to 3 which is other than tetracalcium phosphate, an additional source of calcium selected from the the group consisting of calcium carborate, calcium oxide and calcium hydroxide, and an aqueous phosphate solution of a non-calcium containing salt of phosphoric acid with phosphate concentration of about 0.2 mols/L or above in the absence of solid crystalline phosphoric acid.

12. A calcium phosphate composition, which self-hardens to hydroxyapatite as the predominant product at ambient temperature, comprising a calcium phosphate salt having a calcium to phosphorus molar ratio of less than 5 to 3 which is other than tetracalcium phosphate, an additional source of calcium selected from the group consisting of calcium carbonate, calcium oxide and calcium hydroxide, water and a non-calcium containing salt of phosphoric acid at a concentration of about 0.2 mols/L or above in the absence of solid crystalline phosphoric acid.

13. A self-setting calcium phosphate bone cement comprising a mixture of (1) calcium phosphate salt having a calcium to phosphorus molar ratio of less than 5 to 3 which is other than tetracalcium phosphate, (2) an additional source of calcium selected from the group consisting of calcium carbonate, calcium oxide and calcium hydroxide, and (3) an aqueous phosphate solution of pH of about 12.5 or above with a concentration of phosphate of about 0.2 mols/L or above, in the absence of solid crystalline phosphoric acid.

14. The method of claim 1 wherein the calcium phosphate salt is selected from the group consisting of dicalcium phosphate anhydrous, dicaleium phosphate dihydrate, α-tricalcium phosphate, amorphous calcium phosphate, octacalcium phosphate and β-tricalcium phosphate.

15. The method of claim 1 wherein the base employed to adjust the pH of the solution to about 12.5 or above is sodium hydroxide.

16. The composition of claim 7 further including fluoride containing compounds such that the fluoride content of the composition is in an amount sufficient to increase the rate of formation of hydroxyapatite.

17. The composition of claim 16 wherein the fluoride compounds are selected from the group consisting of NaF, $CaF_2$, $SnF_2$, $Na_2PO_3F$, and $Na_2SiF_6$.

18. The composition of claim 16 wherein the fluoride content in the composition is about 3.8% by weight.

19. The composition in claim 7 further including a seed crystal compound from the group consisting of HA and fluorapatite in an amount sufficient to reduce the setting time of the cement.

20. A calcium phosphate cement that is a tissue substitute having as a calcium phosphate component the composition of claim 7.

21. A calcium phosphate cement that is a tissue substitute having as a calcium phosphate component the composition of claim 9.

22. A calcium phosphate cement that is a tissue substitute having as a calcium phosphate component the composition of claim 11.

23. A calcium phosphate bone cement which self-sets to hydroxyapatite at ambient temperature and is substantially resorbable when implanted in contact with living bone comprising the composition of claim 7.

24. A calcium phosphate bone cement which self-sets to hydroxyapatite at ambient temperature and is substantially resorbable when implanted in contact with living bone comprising the composition of claim 7.

25. A calcium phosphate bone cement which self-sets to hydroxyapatite at ambient temperature and is substantially resorbable when implanted in contact with living bone comprising the composition of claim 11.

26. The composition of claim 7 further comprising an additive selected from the group consisting of medicaments, filler materials, crystal adjustors, viscosity modifiers, pore forming agents, osteoinductive factors, bone morphogenic proteins and other proteins.

27. The composition of claim 26 further including gelling agents.

28. The composition of claim 27 wherein the gelling agents are selected from the group consisting of hydroxypropyl methylcellulose, carboxyl methylcellulose, starch, proteoglycans, glycoproteins.

29. The composition of claim 7 further including medicaments such that the medicaments are released into the suffounding living tissue over a period of time.

30. The composition of claim 7 which includes filler materials in sufficient amounts to increase the strength of the cement.

31. The composition of claim 30 wherein the filler materials are selected from the group of non-toxic biocompatible natural or synthetic polymers and non-toxic biocompatible metal.

32. The composition of claim 7 further including pore forming agents that form pores of a diameter effective to cause vascularization of tissue which infiltrates the composition.

33. The composition of claim 32 wherein the pore forming agents are materials that are sufficiently insoluble in the cement and can be removed by dissolution in physiological fluids, removed by solvents or heating after the hardening of the cement.

* * * * *